(12) United States Patent
Hacohen (10) Patent No.: US 10,610,359 B2
(45) Date of Patent: Apr. 7, 2020

(54) FOLDING RING PROSTHETIC HEART VALVE

(71) Applicant: CARDIOVALVE LTD., Or Yehuda (IL)

(72) Inventor: Gil Hacohen, Ramat Gan (IL)

(73) Assignee: CARDIOVALVE LTD., Or Yehuda (IL)

( * ) Notice: Subject to any disclaimer, the term of this patent is extended or adjusted under 35 U.S.C. 154(b) by 0 days.

(21) Appl. No.: 16/183,140

(22) Filed: Nov. 7, 2018

(65) Prior Publication Data

US 2019/0069998 A1 Mar. 7, 2019

Related U.S. Application Data

(60) Division of application No. 15/188,507, filed on Jun. 21, 2016, now Pat. No. 10,231,831, which is a continuation of application No. 14/522,987, filed on Oct. 24, 2014, now abandoned, which is a continuation of application No. 12/961,721, filed on Dec. 7, 2010, now Pat. No. 8,870,950.

(60) Provisional application No. 61/283,819, filed on Dec. 8, 2009.

(51) Int. Cl.
*A61F 2/24* (2006.01)

(52) U.S. Cl.
CPC .......... *A61F 2/2418* (2013.01); *A61F 2/2409* (2013.01); *A61F 2/2412* (2013.01); *A61F 2/2445* (2013.01); *A61F 2/2439* (2013.01); *A61F 2/2454* (2013.01); *A61F 2/2457* (2013.01); *A61F 2220/0016* (2013.01)

(58) Field of Classification Search
CPC .............................. A61F 2/2418; A61F 2/2445
See application file for complete search history.

(56) References Cited

U.S. PATENT DOCUMENTS

| 4,261,342 A | 4/1981 | Aranguren Duo |
| 4,892,541 A | 1/1990 | Alonso |
| 5,108,420 A | 4/1992 | Marks |
| 5,607,444 A | 3/1997 | Lam |

(Continued)

FOREIGN PATENT DOCUMENTS

| EP | 1264582 A2 | 12/2002 |
| WO | 00/47139 A1 | 8/2000 |

(Continued)

OTHER PUBLICATIONS

U.S. Appl. No. 15/188,507, filed Jun. 21, 2016, published as 2016/0296330.

(Continued)

*Primary Examiner* — Suba Ganesan
(74) *Attorney, Agent, or Firm* — Ladas & Parry LLP; Frank Gao (57) ABSTRACT

Apparatus is provided for use with a prosthetic valve for implantation at a patient's native heart valve. The apparatus includes an implant and a tool. The implant includes a plurality of metal segments coupled at a plurality of joints to define a ring having upper joints and lower joints disposed along the ring. The implant also includes a plurality of anchors coupled to the ring at the joints. The tool is couplable to the implant, and is configured to anchor the implant at the native heart valve by rotation of the tool. Other embodiments are also described.

25 Claims, 3 Drawing Sheets

(56) References Cited

U.S. PATENT DOCUMENTS

| | | | |
|---|---|---|---|
| 5,776,140 A * | 7/1998 | Cottone | |
| 5,868,777 A | 2/1999 | Lam | |
| 5,957,949 A | 9/1999 | Leonhardt et al. | |
| 6,010,530 A | 1/2000 | Goicoechea | |
| 6,042,607 A | 3/2000 | Williamson, IV et al. | |
| 6,074,417 A | 6/2000 | Peredo | |
| 6,113,612 A | 9/2000 | Swanson et al. | |
| 6,120,534 A | 9/2000 | Ruiz | |
| 6,152,937 A | 11/2000 | Peterson et al. | |
| 6,287,339 B1 | 9/2001 | Vazquez et al. | |
| 6,332,893 B1 | 12/2001 | Mortier et al. | |
| 6,391,036 B1 | 5/2002 | Berg et al. | |
| 6,402,780 B2 | 6/2002 | Williamson, IV et al. | |
| 6,409,755 B1 | 6/2002 | Vrba | |
| 6,419,696 B1 | 7/2002 | Ortiz et al. | |
| 6,428,550 B1 | 8/2002 | Vargas et al. | |
| 6,440,164 B1 | 8/2002 | DiMatteo et al. | |
| 6,458,153 B1 | 10/2002 | Bailey et al. | |
| 6,511,491 B2 | 1/2003 | Grudem et al. | |
| 6,540,782 B1 | 4/2003 | Snyders | |
| 6,558,418 B2 | 5/2003 | Carpentier et al. | |
| 6,602,263 B1 | 8/2003 | Swanson et al. | |
| 6,616,675 B1 | 9/2003 | Evard et al. | |
| 6,699,256 B1 | 3/2004 | Logan et al. | |
| 6,716,244 B2 | 4/2004 | Klaco | |
| 6,719,781 B1 | 4/2004 | Kim | |
| 6,730,118 B2 | 5/2004 | Spenser et al. | |
| 6,767,362 B2 | 7/2004 | Schreck | |
| 6,830,638 B2 | 12/2004 | Boylan et al. | |
| 6,951,571 B1 | 10/2005 | Srivastava | |
| 6,960,217 B2 | 11/2005 | Bolduc | |
| 6,964,684 B2 | 11/2005 | Ortiz et al. | |
| 7,011,681 B2 | 3/2006 | Vesely | |
| 7,018,406 B2 | 3/2006 | Seguin et al. | |
| 7,077,861 B2 | 7/2006 | Spence | |
| 7,101,395 B2 | 9/2006 | Tremulis et al. | |
| 7,172,625 B2 | 2/2007 | Shu et al. | |
| 7,198,646 B2 | 4/2007 | Figulla et al. | |
| 7,201,772 B2 | 4/2007 | Schwammenthal et al. | |
| 7,288,111 B1 | 10/2007 | Holloway et al. | |
| 7,404,824 B1 | 7/2008 | Webler et al. | |
| 7,429,269 B2 | 9/2008 | Schwammenthal et al. | |
| 7,442,204 B2 | 10/2008 | Schwammenthal et al. | |
| 7,455,677 B2 | 11/2008 | Vargas et al. | |
| 7,455,688 B2 | 11/2008 | Furst et al. | |
| 7,462,162 B2 | 12/2008 | Phan et al. | |
| 7,481,838 B2 | 1/2009 | Carpentier et al. | |
| 7,510,575 B2 | 3/2009 | Spenser et al. | |
| 7,513,909 B2 | 4/2009 | Lane et al. | |
| 7,527,646 B2 | 5/2009 | Rahdert et al. | |
| 7,582,111 B2 | 9/2009 | Krolik et al. | |
| 7,585,321 B2 | 9/2009 | Cribier | |
| 7,632,302 B2 | 12/2009 | Vreeman et al. | |
| 7,708,775 B2 | 5/2010 | Rowe et al. | |
| 7,717,955 B2 | 5/2010 | Lane et al. | |
| 7,731,741 B2 | 6/2010 | Eidenschink | |
| 7,753,922 B2 | 7/2010 | Starksen | |
| 7,771,467 B2 | 8/2010 | Svensson | |
| 7,771,469 B2 | 8/2010 | Liddicoat | |
| 7,780,726 B2 | 8/2010 | Seguin | |
| 7,799,069 B2 | 9/2010 | Bailey et al. | |
| 7,803,181 B2 | 9/2010 | Furst et al. | |
| 7,837,727 B2 | 11/2010 | Goetz et al. | |
| 7,842,081 B2 | 11/2010 | Yadin | |
| 7,850,725 B2 | 12/2010 | Vardi et al. | |
| 7,871,432 B2 | 1/2011 | Bergin | |
| 7,871,436 B2 | 1/2011 | Ryan et al. | |
| 7,887,583 B2 | 2/2011 | Macoviak | |
| 7,892,281 B2 | 2/2011 | Seguin et al. | |
| 7,896,915 B2 | 3/2011 | Guyenot et al. | |
| 7,914,544 B2 | 3/2011 | Nguyen et al. | |
| 7,914,569 B2 | 3/2011 | Nguyen et al. | |
| 7,947,072 B2 | 5/2011 | Yang et al. | |
| 7,947,075 B2 | 5/2011 | Goetz et al. | |
| 7,955,375 B2 | 6/2011 | Agnew | |
| 7,955,384 B2 | 6/2011 | Rafiee et al. | |
| 7,967,833 B2 | 6/2011 | Sterman et al. | |
| 7,981,151 B2 | 7/2011 | Rowe | |
| 7,981,153 B2 | 7/2011 | Fogarty et al. | |
| 7,993,393 B2 | 8/2011 | Carpentier et al. | |
| 8,002,825 B2 | 8/2011 | Letac et al. | |
| 8,016,877 B2 | 9/2011 | Seguin et al. | |
| 8,016,882 B2 | 9/2011 | Macoviak et al. | |
| 8,021,420 B2 | 9/2011 | Dolan | |
| 8,021,421 B2 | 9/2011 | Fogarty et al. | |
| 8,029,564 B2 | 10/2011 | Johnson et al. | |
| 8,034,104 B2 | 10/2011 | Carpentier et al. | |
| 8,043,360 B2 | 10/2011 | McNamara et al. | |
| 8,048,140 B2 | 11/2011 | Purdy | |
| 8,048,153 B2 | 11/2011 | Salahieh et al. | |
| 8,057,532 B2 | 11/2011 | Hoffman | |
| 8,057,540 B2 | 11/2011 | Letac et al. | |
| 8,062,355 B2 | 11/2011 | Figulla et al. | |
| 8,062,359 B2 | 11/2011 | Marquez et al. | |
| 8,070,708 B2 | 12/2011 | Rottenberg et al. | |
| 8,070,802 B2 | 12/2011 | Lamphere et al. | |
| 8,075,611 B2 | 12/2011 | Millwee et al. | |
| 8,080,054 B2 | 12/2011 | Rowe | |
| 8,092,518 B2 | 1/2012 | Schreck | |
| 8,092,520 B2 | 1/2012 | Quadri | |
| 8,092,521 B2 | 1/2012 | Figulla et al. | |
| 8,105,377 B2 | 1/2012 | Liddicoat | |
| 8,118,866 B2 | 2/2012 | Herrmann et al. | |
| 8,136,218 B2 | 3/2012 | Millwee et al. | |
| 8,137,398 B2 | 3/2012 | Tuval et al. | |
| 8,142,494 B2 | 3/2012 | Rahdert et al. | |
| 8,142,496 B2 | 3/2012 | Berreklouw | |
| 8,142,497 B2 | 3/2012 | Friedman | |
| 8,147,504 B2 | 4/2012 | Ino et al. | |
| 8,157,852 B2 | 4/2012 | Bloom et al. | |
| 8,157,853 B2 | 4/2012 | Laske et al. | |
| 8,157,860 B2 | 4/2012 | McNamara et al. | |
| 8,163,014 B2 | 4/2012 | Lane et al. | |
| 8,167,894 B2 | 5/2012 | Miles et al. | |
| 8,167,932 B2 | 5/2012 | Bourang et al. | |
| 8,172,896 B2 | 5/2012 | McNamara et al. | |
| 8,177,836 B2 | 5/2012 | Lee et al. | |
| 8,182,528 B2 | 5/2012 | Salahieh et al. | |
| 8,211,169 B2 | 7/2012 | Lane et al. | |
| 8,221,492 B2 | 7/2012 | Case et al. | |
| 8,221,493 B2 | 7/2012 | Boyle et al. | |
| 8,226,710 B2 | 7/2012 | Nguyen et al. | |
| 8,231,670 B2 | 7/2012 | Salahieh et al. | |
| 8,236,045 B2 | 8/2012 | Benichou et al. | |
| 8,252,042 B2 | 8/2012 | McNamara et al. | |
| 8,252,051 B2 | 8/2012 | Chau et al. | |
| 8,252,052 B2 | 8/2012 | Salahieh et al. | |
| 8,257,390 B2 | 9/2012 | Carley et al. | |
| 8,277,501 B2 | 10/2012 | Chalekian et al. | |
| 8,287,591 B2 | 10/2012 | Keidar et al. | |
| 8,298,280 B2 | 10/2012 | Yadin et al. | |
| 8,308,798 B2 | 11/2012 | Pintor et al. | |
| 8,317,855 B2 | 11/2012 | Gregorich et al. | |
| 8,323,335 B2 | 12/2012 | Rowe et al. | |
| 8,328,868 B2 | 12/2012 | Paul et al. | |
| 8,343,174 B2 | 1/2013 | Goldfarb et al. | |
| 8,628,571 B1 | 1/2014 | Hacohen et al. | |
| 8,728,155 B2 | 5/2014 | Montorfano et al. | |
| 8,852,272 B2 | 10/2014 | Gross et al. | |
| 8,870,948 B1 | 10/2014 | Erzbarger et al. | |
| 9,095,434 B2 | 8/2015 | Rowe | |
| 9,232,995 B2 | 1/2016 | Kovalsky et al. | |
| 9,248,014 B2 | 2/2016 | Lane et al. | |
| 9,439,757 B2 | 9/2016 | Wallace et al. | |
| 9,492,273 B2 | 11/2016 | Wallace et al. | |
| 9,554,899 B2 | 1/2017 | Granada et al. | |
| 9,561,103 B2 | 2/2017 | Granada et al. | |
| 9,763,657 B2 | 9/2017 | Hacohen et al. | |
| 9,788,941 B2 | 10/2017 | Hacohen | |
| 10,143,552 B2 | 12/2018 | Wallace et al. | |
| 10,149,761 B2 | 12/2018 | Granada et al. | |
| 10,154,906 B2 | 12/2018 | Granada et al. | |
| 10,182,908 B2 | 1/2019 | Tubishevitz et al. | |
| 10,226,341 B2 | 3/2019 | Gross et al. | |

(56) References Cited

U.S. PATENT DOCUMENTS

| | | |
|---|---|---|
| 10,245,143 B2 | 4/2019 | Gross et al. |
| 10,376,161 B2 | 8/2019 | Gross et al. |
| 2001/0002445 A1 | 5/2001 | Vesely |
| 2001/0021872 A1 | 9/2001 | Bailey et al. |
| 2002/0032481 A1* | 3/2002 | Gabbay |
| 2002/0151970 A1 | 10/2002 | Garrison et al. |
| 2003/0036791 A1 | 2/2003 | Philipp et al. |
| 2003/0074052 A1 | 4/2003 | Besselink |
| 2003/0105519 A1 | 6/2003 | Fasol et al. |
| 2003/0158578 A1 | 8/2003 | Pantages et al. |
| 2004/0039414 A1 | 2/2004 | Carley et al. |
| 2004/0093060 A1 | 5/2004 | Seguin et al. |
| 2004/0122514 A1 | 6/2004 | Fogarty et al. |
| 2004/0176839 A1 | 9/2004 | Huynh et al. |
| 2004/0186558 A1* | 9/2004 | Pavcnik et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0225354 A1 | 11/2004 | Allen et al. |
| 2004/0249433 A1 | 12/2004 | Freitag |
| 2004/0260389 A1 | 12/2004 | Case et al. |
| 2005/0004668 A1 | 1/2005 | Aklog et al. |
| 2005/0137688 A1 | 6/2005 | Salahieh et al. |
| 2005/0137690 A1 | 6/2005 | Salahieh et al. |
| 2005/0137695 A1 | 6/2005 | Salahieh et al. |
| 2005/0197695 A1 | 9/2005 | Stacohino et al. |
| 2005/0203549 A1 | 9/2005 | Realyvasquez |
| 2005/0216079 A1 | 9/2005 | MaCoviak |
| 2005/0234508 A1 | 10/2005 | Cummins et al. |
| 2005/0251251 A1 | 11/2005 | Cribier |
| 2006/0004469 A1 | 1/2006 | Sokel |
| 2006/0047297 A1 | 3/2006 | Case |
| 2006/0052867 A1 | 3/2006 | Revuelta et al. |
| 2006/0135964 A1 | 6/2006 | Vesely |
| 2006/0178740 A1 | 8/2006 | Stacchino et al. |
| 2006/0190036 A1 | 8/2006 | Wendel et al. |
| 2006/0190038 A1 | 8/2006 | Carley et al. |
| 2006/0195184 A1 | 8/2006 | Lane et al. |
| 2006/0201519 A1 | 9/2006 | Frazier et al. |
| 2006/0241656 A1 | 10/2006 | Starksen et al. |
| 2006/0241745 A1 | 10/2006 | Solem |
| 2006/0241748 A1 | 10/2006 | Lee et al. |
| 2006/0247680 A1 | 11/2006 | Amplatz et al. |
| 2006/0253191 A1 | 11/2006 | Salahleh et al. |
| 2006/0259136 A1 | 11/2006 | Nguyen et al. |
| 2006/0271166 A1 | 11/2006 | Thill |
| 2007/0016288 A1 | 1/2007 | Gurskis |
| 2007/0038295 A1 | 2/2007 | Case et al. |
| 2007/0043435 A1 | 2/2007 | Seguin et al. |
| 2007/0056346 A1 | 3/2007 | Spenser et al. |
| 2007/0078510 A1 | 4/2007 | Ryan |
| 2007/0112422 A1 | 5/2007 | Dehdashtian |
| 2007/0118151 A1 | 5/2007 | Davidson |
| 2007/0162107 A1 | 7/2007 | Haug et al. |
| 2007/0162111 A1 | 7/2007 | Fukamachi et al. |
| 2007/0198077 A1 | 8/2007 | Cully et al. |
| 2007/0213810 A1 | 9/2007 | Newhauser et al. |
| 2007/0213813 A1 | 9/2007 | Von Segesser |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0239272 A1 | 10/2007 | Navia et al. |
| 2007/0255400 A1 | 11/2007 | Parravicini et al. |
| 2008/0004688 A1 | 1/2008 | Spenser et al. |
| 2008/0004697 A1 | 1/2008 | Lichtenstein et al. |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0077235 A1 | 3/2008 | Kirson |
| 2008/0086164 A1 | 4/2008 | Rowe |
| 2008/0086204 A1 | 4/2008 | Rankin |
| 2008/0147182 A1 | 6/2008 | Righini et al. |
| 2008/0161910 A1 | 7/2008 | Revuelta et al. |
| 2008/0167714 A1 | 7/2008 | St. Goar et al. |
| 2008/0195200 A1 | 8/2008 | Vidlund et al. |
| 2008/0208332 A1 | 8/2008 | Lamphere et al. |
| 2008/0221672 A1 | 9/2008 | Lamphere et al. |
| 2008/0243245 A1 | 10/2008 | Thambar et al. |
| 2008/0262609 A1 | 10/2008 | Gross et al. |
| 2008/0281411 A1 | 11/2008 | Berreklouw |
| 2009/0005863 A1 | 1/2009 | Goetz et al. |
| 2009/0054969 A1 | 2/2009 | Salahieh et al. |
| 2009/0125098 A1 | 5/2009 | Chuter |
| 2009/0157175 A1 | 6/2009 | Benichou |
| 2009/0177278 A1 | 7/2009 | Spence |
| 2009/0210052 A1 | 8/2009 | Forster et al. |
| 2009/0264994 A1 | 10/2009 | Saadat |
| 2009/0319037 A1 | 12/2009 | Rowe et al. |
| 2010/0023117 A1 | 1/2010 | Yoganathan et al. |
| 2010/0023120 A1 | 1/2010 | Holecek et al. |
| 2010/0036479 A1 | 2/2010 | Hill et al. |
| 2010/0076548 A1 | 3/2010 | Konno |
| 2010/0100167 A1 | 4/2010 | Bortlein et al. |
| 2010/0114299 A1 | 5/2010 | Ben Muvhar et al. |
| 2010/0131054 A1 | 5/2010 | Tuval et al. |
| 2010/0137979 A1 | 6/2010 | Tuval et al. |
| 2010/0160958 A1 | 6/2010 | Clark |
| 2010/0161036 A1 | 6/2010 | Pintor et al. |
| 2010/0161042 A1 | 6/2010 | Maisano et al. |
| 2010/0174363 A1 | 7/2010 | Castro |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0222810 A1 | 9/2010 | DeBeer et al. |
| 2010/0228285 A1 | 9/2010 | Miles et al. |
| 2010/0234940 A1 | 9/2010 | Dolan |
| 2010/0249908 A1 | 9/2010 | Chau et al. |
| 2010/0249917 A1 | 9/2010 | Zhang |
| 2010/0262232 A1 | 10/2010 | Annest |
| 2010/0280606 A1 | 11/2010 | Naor |
| 2010/0312333 A1 | 12/2010 | Navia et al. |
| 2010/0324595 A1 | 12/2010 | Linder et al. |
| 2010/0331971 A1 | 12/2010 | Keranen et al. |
| 2011/0004296 A1 | 1/2011 | Lutter et al. |
| 2011/0015729 A1 | 1/2011 | Jimenez et al. |
| 2011/0015731 A1 | 1/2011 | Carpentier et al. |
| 2011/0022165 A1 | 1/2011 | Oba et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0082538 A1 | 4/2011 | Dahlgren et al. |
| 2011/0087322 A1 | 4/2011 | Letac et al. |
| 2011/0093063 A1 | 4/2011 | Schreck |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0118830 A1 | 5/2011 | Liddicoat et al. |
| 2011/0125257 A1 | 5/2011 | Seguin et al. |
| 2011/0137397 A1* | 6/2011 | Chau ............... A61F 2/2418 623/1.11 |
| 2011/0137409 A1 | 6/2011 | Yang et al. |
| 2011/0144742 A1 | 6/2011 | Madrid et al. |
| 2011/0166636 A1 | 7/2011 | Rowe |
| 2011/0172784 A1 | 7/2011 | Richter et al. |
| 2011/0178597 A9 | 7/2011 | Navia et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0208283 A1 | 8/2011 | Rust |
| 2011/0208293 A1 | 8/2011 | Tabor |
| 2011/0208298 A1 | 8/2011 | Tuval et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251679 A1 | 10/2011 | Wiemeyer et al. |

(56) References Cited

U.S. PATENT DOCUMENTS

| | | |
|---|---|---|
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257721 A1 | 10/2011 | Tabor |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung et al. |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy et al. |
| 2011/0270276 A1 | 11/2011 | Rothstein et al. |
| 2011/0271967 A1 | 11/2011 | Mortier et al. |
| 2011/0282438 A1 | 11/2011 | Drews et al. |
| 2011/0283514 A1 | 11/2011 | Fogarty et al. |
| 2011/0288632 A1 | 11/2011 | White |
| 2011/0288634 A1 | 11/2011 | Tuval et al. |
| 2011/0301688 A1 | 12/2011 | Dolan |
| 2011/0301702 A1 | 12/2011 | Rust et al. |
| 2011/0313452 A1 | 12/2011 | Carley et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0022637 A1 | 1/2012 | Ben-Muvhar |
| 2012/0022639 A1 | 1/2012 | Hacohen et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0089223 A1 | 4/2012 | Nguyen et al. |
| 2012/0310328 A1 | 12/2012 | Olson et al. |
| 2013/0035759 A1 | 2/2013 | Gross et al. |
| 2013/0190861 A1 | 7/2013 | Chau et al. |
| 2013/0261733 A1 | 10/2013 | Clague et al. |
| 2013/0304200 A1 | 11/2013 | McLean et al. |
| 2014/0005778 A1 | 1/2014 | Buchbinder et al. |
| 2014/0142688 A1 | 5/2014 | Duffy et al. |
| 2014/0172077 A1 | 6/2014 | Bruchman et al. |
| 2014/0172082 A1 | 6/2014 | Bruchman et al. |
| 2014/0222136 A1 | 8/2014 | Geist et al. |
| 2014/0249622 A1 | 9/2014 | Carmi et al. |
| 2014/0277418 A1 | 9/2014 | Miller |
| 2015/0142100 A1 | 5/2015 | Morriss et al. |
| 2015/0173897 A1 | 6/2015 | Raanani et al. |
| 2015/0351903 A1 | 12/2015 | Morriss et al. |
| 2015/0351904 A1 | 12/2015 | Cooper et al. |
| 2016/0030169 A1 | 2/2016 | Shahriari |
| 2016/0125160 A1 | 5/2016 | Heneghan et al. |
| 2016/0324635 A1 | 11/2016 | Vidlund et al. |
| 2016/0331527 A1 | 11/2016 | Vidlund et al. |
| 2016/0374801 A1 | 12/2016 | Jimenez et al. |
| 2017/0056166 A1 | 3/2017 | Ratz et al. |
| 2018/0296341 A1 | 10/2018 | Noe et al. |
| 2018/0344457 A1 | 12/2018 | Gross et al. |

FOREIGN PATENT DOCUMENTS

| | | |
|---|---|---|
| WO | 01/62189 A1 | 8/2001 |
| WO | 2005/107650 A2 | 11/2005 |
| WO | 2006/054930 A1 | 5/2006 |
| WO | 2008/013915 A3 | 1/2008 |
| WO | 2009/003469 A1 | 3/2009 |
| WO | 2009/053497 A1 | 4/2009 |
| WO | 2010/006627 A1 | 1/2010 |
| WO | 2010/037141 A1 | 4/2010 |
| WO | 2010/057262 A1 | 5/2010 |
| WO | 2010/121076 A2 | 10/2010 |
| WO | 2011/106137 A1 | 9/2011 |
| WO | 2011/111047 A2 | 9/2011 |
| WO | 2011/143263 A2 | 11/2011 |
| WO | 2012/011108 A2 | 1/2012 |
| WO | 2012/048035 A2 | 4/2012 |
| WO | 2013/021374 A2 | 2/2013 |
| WO | 2013/021375 A2 | 2/2013 |
| WO | 2013/078497 A1 | 6/2013 |
| WO | 2013/175468 | 11/2013 |
| WO | 2014/0164364 A1 | 10/2014 |
| WO | 2014/194178 A1 | 12/2014 |
| WO | 2016/125160 A1 | 8/2016 |
| WO | 2018/029680 A1 | 2/2018 |
| WO | 2018/039631 A1 | 3/2018 |

OTHER PUBLICATIONS

U.S. Appl. No. 61/283,819, filed Dec. 8, 2009.

U.S. Appl. No. 14/522,987, filed Oct. 24, 2014, published as 2015/0045880.

U.S. Appl. No. 12/961,721, filed Dec. 7, 2010, published as 2011/0137410, now U.S. Pat. No. 8,870,950.

Extended European Search Report dated Sep. 26, 2018; Appln, No. 18186784.7.

The First Chinese Office Action dated Nov. 5, 2018; Appln. No. 201680008328.5.

Invitation to pay additional fees dated Oct. 11, 2018; PCT/IL2018/050725.

USPTO NFOA dated Dec. 4, 2018 in connection with U.S. Appl. No. 16/045,059.

USPTO NOA dated Sep. 25, 2018 in connection with U.S. Appl. No. 15/188,507.

Alexander S. Geha, et al; "Replacement of degenerated mitral and aortic bioprostheses without explanation", Ann Thorac Surg, Nov. 2001; vol. 72, pp. 1509-1514.

Josef Jansen, et al; "Detachable Shape-Memory Sewing Ring for Heart Valves", Artificial Organ, vol. 16, No. 3, Jun. 1992, pp. 294-297.

Frank Lancer et al; "RING plus STRING: Papillary muscle repositioning as an adjunctive repair technique for ischemic mitral regurgitation", J. Thorac Cardiovasc Surg 2007; 133:247-247, online version of this article with updated information and services is located on the World Wide Web at: http://jtcs.ctsnetjournals.org/cgi/content/full/133/1/247.

Frank Langer et al; "RING + STRING: Successful Repair Technique for Ischemic Mitral Regurgitation With Severe Leaflet Tethering"; Circulation 120 [supp 1]: S85-S91; Sep. 15, 2009.

John G. Webb et al; "Transcatheter Valve-in-Valve Implantation for Failed Bioprosthetic Heart VAlves", Circulation, 2010; vol. 121; pp. 1848-1857; originally published online Apr. 12, 2010.

ISR & WO dated Oct. 13, 2011; PCT/IL/00231.

ISR & WO dated Dec. 5, 2011; PCT/IL/00582.

ISR & WO dated Feb. 6, 2013; PCT/IL12/00292.

ISR & WO dated Feb. 6, 2013; PCT/IL12/00293.

USPTO NFOA dated May 29, 2012 in connection with U.S. Appl. No. 12/840,463.

USPTO FOA dated Feb. 15, 2013 in connection with U.S. Appl. No. 12/840,463.

USPTO NFOA dated Nov. 23, 2012 in connection with U.S. Appl. No. 13/033,852.

USPTO NFOA dated Dec. 31, 2012 in connection with U.S. Appl. No. 13/044,694.

USPTO NFOA dated Feb. 6, 2013 in connection with U.S. Appl. No. 13/412,814.

An International Search Report and a Written Opinion both dated May 13, 2019, which issued during the prosecution of Applicant's PCT/IL2018/051350.

An International Search Report and a Written Opinion both dated Apr. 5, 2019, which issued during the prosecution of Applicants's PCT/IL2019/050142.

(56) References Cited

OTHER PUBLICATIONS

An international Search Report and a Written Opinion both dated Jan. 25, 2019, which issued during the prosecution of Applicant's PCT/IL2018/051122.
An International Search Report and a Written Opinion both dated Dec. 5, 2018, which issued during the prosecution of Applicant's PCT/IL2018/050725.
An International Preliminary Report on Patentability dated Feb. 12, 2019, which issued during the prosecution of Applicant's PCT/IL2017/050873.
An International Preliminary Report on Patentability dated Feb. 5, 2019, which issued during the prosecution of Applicant's PCT/IL2017/050849.
An Office Action dated Mar. 25, 2019, which issued during the prosecution of European Patent Application No. 14710060.6.
An Office Action dated Oct. 25, 2018, which issued during the prosecution of U.S. Appl. No. 14/763,004.
An Office Action dated Mar. 4, 2019, which issued during the prosecution of U.S. Appl. No. 14/763,004.
An Office Action dated Jan. 9, 2019, which issued during the prosecution of U.S. Appl. No. 15/329,920.
An Office Action dated Jan. 30, 2019, which issued during the prosecution of U.S. Appl. No. 15/872,501.
An Office Action dated Feb. 5, 2019, which issued during the prosecution of U.S. Appl. No. 15/899,858.
An Office Action dated May 23, 2019, which issued during the prosecution of U.S. Appl. No. 15/668,659.
An Office Action dated May 1, 2019, which issued during the prosecution of U.S. Appl. No. 15/691,032.
An International Search Report and a Written Opinion both dated Nov. 9, 2018, which issued during the prosecution of Applicant's PCT/IL2018/050869.
An Office Action dated Jun. 25, 2019, which is issued during the prosecution of U.S. Appl. No. 15/329,920.
An Office Action dated May 16, 2019, which issued during the prosecution of U.S. Appl. No. 15/433,547.
An Office Action dated Aug. 1, 2019, which issued during the prosecution of U.S. Appl. No. 15/668,559.
An Office Action dated Aug. 16, 2019, which issued during the prosecution of U.S. Appl. No. 15/668,659.
An Office Action dated Jun. 19, 2019, which issued during the prosecution of U.S. Appl. No. 15/682,789.
An Office Action dated Jun. 14, 2019, which issued during the prosecution of U.S. Appl. No. 15/703,385.
An Office Action dated Nov. 1, 2019, which issued during the prosecution of U.S. Appl. No. 15/872,501.
An Office Action dated Jun. 13, 2019, which issued during the prosecution of U.S. Appl. No. 16/388,038.
An Office Action dated Sep. 13, 2019, which issued during the prosecution of U.S. Appl. No. 16/460,313.
An Office Action Nov. 26, 2019, which issued during the prosecution of U.S. Appl. No. 16/532,945.

* cited by examiner

FOLDING RING PROSTHETIC HEART VALVE

CROSS REFERENCES TO RELATED APPLICATIONS

The present application is a Divisional of U.S. Ser. No. 15/188,507 to HaCohen, filed Jun. 21, 2016, and entitled "FOLDING RING IMPLANT FOR HEART VALVE," which published as US 2016/0296330 (now U.S. Pat. No. 10,231,831), and which is a Continuation of U.S. Ser. No. 14/522,987 to HaCohen, filed Oct. 24, 2014, and entitled "IMPLANT FOR ROTATION-BASED ANCHORING," which published as US 2015/0045880 (abandoned), and which is a Continuation of U.S. Ser. No. 12/961,721 to HaCohen, filed Dec. 7, 2010, and entitled "ROTATION-BASED ANCHORING OF AN IMPLANT," which published as 2011/0137410 (now U.S. Pat. No. 8,870,950), which claims the benefit of U.S. Provisional Patent Application 61/283,819, entitled "FOLDABLE HINGED PROSTHETIC HEART VALVE," to Hacohen, filed Dec. 8, 2009, which is incorporated herein by reference.

FIELD OF EMBODIMENTS OF THE INVENTION

Embodiments of the present invention relates in general to valve replacement. More specifically, embodiments of the present invention relate to replacement of an atrioventricular valve and prosthetic valve therefor.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF EMBODIMENTS

In some applications of the present invention, a prosthetic heart valve structure is provided that collapses and expands by means of one or more valve pivot joints. The prosthetic valve structure is typically designated for implantation in a native atrioventricular valve site of a heart of a patient, although for some applications, the prosthetic valve structure is designated for implantation at the aortic or tricuspid valve. The prosthetic valve structure comprises an annular ring portion that is designated for placement adjacent to the ventricular surface of the native valve of the patient. This annular ring portion comprises the valve pivot joints, which facilitate collapsing of the prosthetic valve structure for transcatheter advancement of the valve toward the heart of the patient. Additionally, the annular portion of the prosthetic valve structure is coupled to a plurality of anchors which are configured to grasp the native chordae tendineae of the heart of the patient. These anchors comprise generally curved prong structures which, in an expanded state of the prosthetic valve structure, are aligned circumferentially along the annular ring portion of the prosthetic valve structure (generally perpendicular to a radius of the annular ring portion). Once the annular ring portion is positioned adjacent to the ventricular surface of the native mitral valve, the prosthetic valve structure is rotated, in order for the anchors to engage the native chordae tendineae. During the engaging, portions of the native chordae tendineae are gathered between each anchor and a respective portion of the annular ring. This engaging provides support to the prosthetic valve structure as it is positioned in and replaces the native valve. Additionally, the prosthetic valve structure comprises ventricular and atrial skirts which provide flush positioning of the prosthetic valve in the native valve.

There is therefore provided, in accordance with some applications of the present invention, apparatus for use with a prosthetic valve that is designated for implantation at a native heart valve of a patient, including:

a valve ring having a plurality of ring segments, each of the segments being hingedly coupled to at least one adjacent segment at a pivot joint, the valve ring being configured:
to be placed adjacent to a surface of the native heart valve, the prosthetic valve having been coupled to the valve ring,
in an expanded state thereof, to define a ring, all of the pivot joints being disposed in a plane that is perpendicular to a longitudinal axis of the ring, and
to be foldable from the expanded state into a shape that has a generally circular cross-section that defines and surrounds at least in part a central lumen, by folding the segments with respect to each other, at the pivot joints.

For some applications, the segments of the ring are configured to become at least partially twisted due to the ring being folded from the expanded state.

For some applications, the prosthetic valve includes a trileaflet valve, and the ring has a number of ring segments that is a multiple of six.

For some applications, the ring has exactly six segments.

For some applications, the prosthetic valve includes a bileaflet valve, and the ring has a number of ring segments that is a multiple of four.

For some applications, the ring has exactly four segments.

There is further provided, in accordance with some applications of the present invention, a method for use with a prosthetic valve that is designated for implantation at a native heart valve of a patient, including:

placing in a vicinity a surface of the native heart valve, a valve ring that is coupled to the valve, while the valve ring is in a folded state thereof,
the ring having a plurality of ring segments, each of the segments being hingedly coupled to at least one adjacent segment at a pivot joint,
in the folded state thereof, the ring having a shape that has a generally circular cross-section that defines and surrounds at least in part a central lumen;
expanding the ring such that all of the pivot joints become disposed in a plane that is perpendicular to a longitudinal axis of the ring, by applying a force to at least some of the pivot joints; and
when the ring is in an expanded state thereof, positioning the ring adjacent to a surface of the native valve.

For some applications, applying the force to some of the pivot joints includes pushing on pivot joints that are disposed on a proximal side of the ring, while the ring is in the folded state thereof.

For some applications, the native valve includes a native mitral valve, and positioning the ring adjacent to the surface of the valve includes positioning the ring adjacent to a ventricular surface of the native mitral valve.

There is additionally provided, in accordance with some applications of the present invention, apparatus for use with a prosthetic valve that is designated for implantation at a native mitral valve of a patient, including:

an annular ring configured to be placed at a ventricular surface of the native mitral valve, the prosthetic valve having been coupled to the annular ring; and at least one anchor disposed circumferentially with respect to the annular ring so as to define a space between the anchor and the annular ring.

For some applications, the anchor is configured to grasp a portion of native chordae tendineae of a heart of the patient by the annular ring being rotated.

For some applications, the annular ring is configured to be collapsible.

For some applications, the ring includes a plurality of ring segments, each of the segments being hingedly coupled to at least one adjacent segment at a pivot joint, and the ring is configured to be collapsed by folding the segments with respect to each other, at the pivot joints.

There is further provided, in accordance with some applications of the present invention, a method, including:

positioning an annular ring portion of a prosthetic valve structure at a ventricular surface of a native heart valve of a patient; and grasping a portion of native chordae tendineae of a heart of the patient by rotating the annular ring portion of the prosthetic valve structure.

In some applications of the present invention, grasping the portion of the native chordae tendineae includes facilitating placing the portion of the native chordae tendineae in a space between a segment of the annular ring portion and an anchor disposed circumferentially with respect to the segment of the annular ring portion.

In some applications of the present invention, positioning the annular ring portion includes:

transcatheterally advancing the prosthetic valve structure toward the native valve of the patient in a collapsed state thereof; and expanding the prosthetic valve structure from the collapsed state.

In some applications of the present invention, expanding the prosthetic valve structure includes pivoting a plurality of segments of the annular ring portion at respective pivot joints that couple together adjacent segments of the annular ring portion.

The present invention will be more fully understood from the following detailed description of embodiments thereof, taken together with the drawings, in which:

DETAILED DESCRIPTION OF THE EMBODIMENTS

Reference is now made to FIGS. 1-4, which are schematic illustrations of an expandable and collapsible prosthetic valve structure 20, in accordance with some applications of the present invention. The prosthetic valve structure is configured for implantation in and replacement of a native atrioventricular valve of a patient. Typically, the prosthetic valve structure is configured for implantation in and replacement of a native mitral valve of the patient.

The prosthetic valve structure comprises an annular valve ring 24, which comprises a plurality of curved metal segments 26 and a plurality of pivot joints 30 which facilitate the collapsing and expanding of the prosthetic valve structure. The annular valve ring is typically surrounded by a valve ring fabric sleeve 34 comprising a braided mesh of fabric, e.g., Dacron. This sleeve promotes fibrosis following implantation of the prosthetic valve structure in the native valve of the patient. The annular valve ring is coupled to a prosthetic valve that includes a plurality of valve leaflets 44. The valve leaflets are coupled to a flexible valve leaflet frame 40 (e.g., comprising nitinol, by way of illustration and not limitation), which is, in turn, coupled to a valve leaflet frame fabric 42. Typically, the valve leaflet frame fabric (e.g., a fabric comprising Dacron) is coupled to (for example, sutured to) valve ring fabric sleeve 34.

For embodiments in which the prosthetic valve is designated to replace the native mitral valve of the patient, the prosthetic valve comprises three artificial or tissue-based leaflets 44a, 44b, and 44c (shown in FIG. 4), which are coupled to the inner perimeter of the annular valve ring. For example, the leaflets may include pericardium, a polymer, and/or other materials, as would be obvious to one skilled in the art.

Figure 4:
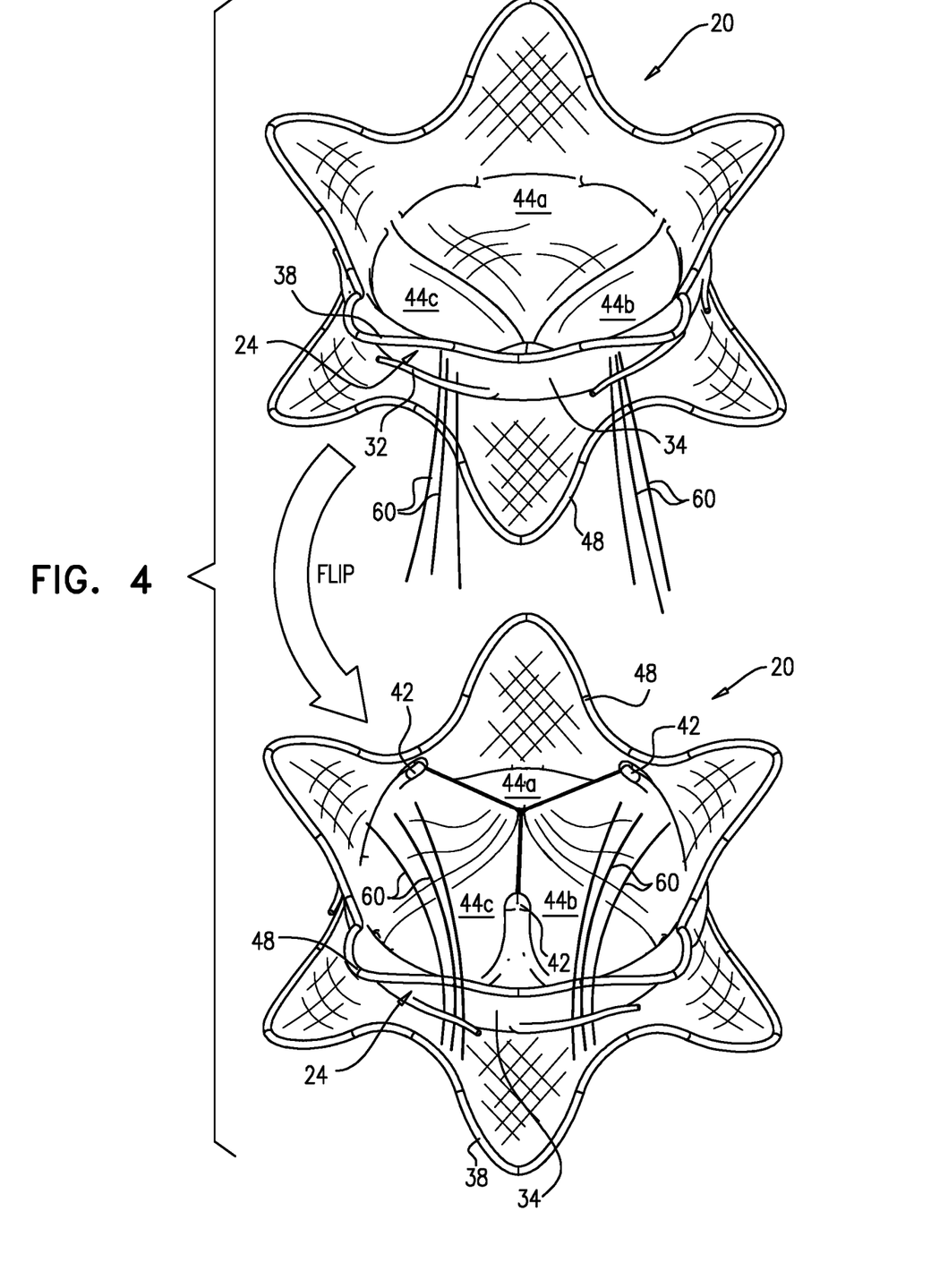
FIG. 4 is a schematic illustration of respective views of the prosthetic heart valve of FIG. 1, while anchors of the valve are anchoring the valve to chordae tendineae of a subject, in accordance with some applications of the present invention.

The annular valve ring portion of the prosthetic valve structure is coupled: (1) at a first surface thereof to an upper skirt, which comprises an upper skirt fabric 38 coupled to a flexible upper skirt frame 36, and (2) at a second surface thereof to a lower skirt, which comprises a lower skirt fabric 48 coupled to a flexible lower skirt frame 46. Typically, the upper and lower frames comprise a flexible material, e.g., nitinol by way of illustration and not limitation. Typically, when the prosthetic valve structure is implanted in the expanded state, as shown in FIG. 4:

(a) the annular valve ring portion is configured to be disposed at a ventricular surface of the native valve, (b) the upper skirt is designated to rest against an atrial portion of the native mitral valve, and (c) the lower skirt is designated to rest against a ventricular surface of the native valve and to push radially the native leaflets of the native valve.

Figure 1:
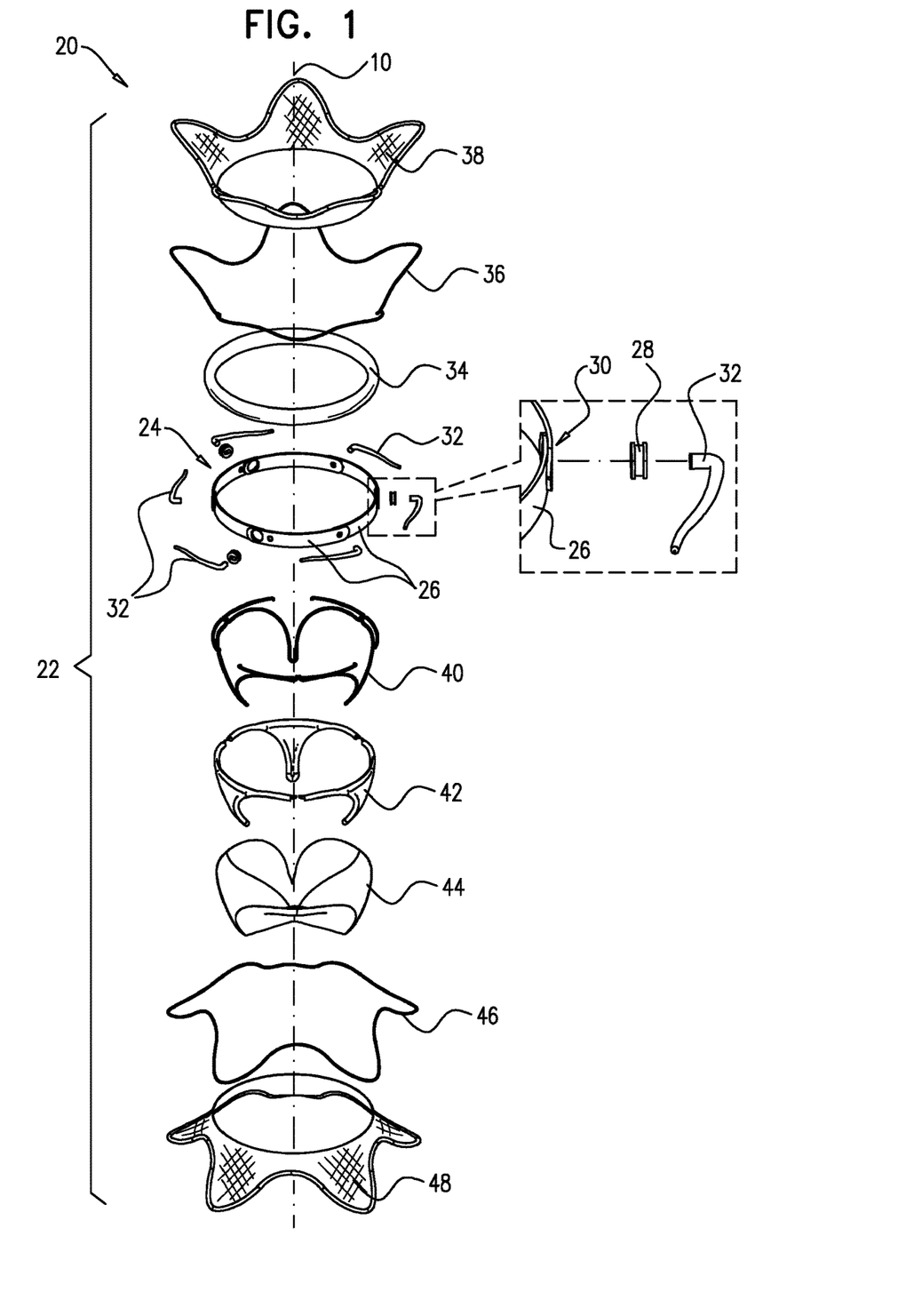
FIG. 1 is a schematic illustration of an exploded view of a prosthetic heart valve, in accordance with some applications of the present invention.
Figure 2A:
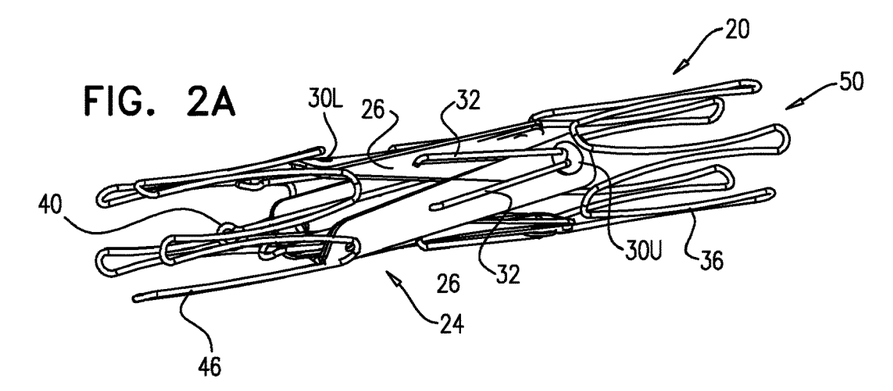
FIGS. 2A-B are schematic illustrations of the prosthetic heart valve of FIG. 1 in an assembled, collapsed state, in accordance with some applications of the present invention.

FIG. 1 shows components 22 of valve structure 20 in an exploded view. Each segment 26 of annular valve ring 24 is coupled at its respective ends to respective ends of adjacent segments via a hinge. For example, as shown, the hinge may include a connecting element 28 that is inserted into holes in the ends of the adjacent segments, such that the adjacent segments form a pivot joint 30. The pivot joints of the ring portion enable the entire prosthetic valve structure to pivot into a collapsed state, the collapsed state being shown in FIGS. 2A-B. Typically, the valve comprises: (a) three "upper" valve pivot joints 30U (shown in FIG. 2A) which are disposed at 120 degrees along the annular valve ring and are near the upper skirt frame 36, in the collapsed state of the valve, shown in FIG. 2A; and (b) three "lower" valve pivot joints 30L (shown in FIG. 2A) also disposed with a separation therebetween of 120 degrees, alternating with the upper valve pivot joints. The lower valve pivot joints are near the lower skirt frame 46, in the collapsed state of the valve as shown in FIG. 2A. The upper valve pivot joints are exposed at a proximal portion of the valve in the collapsed state of the valve (i.e., adjacent to an upper skirt region of the prosthetic valve structure, as shown in FIG. 2A), such that a physician is able to push on the upper valve pivot joints with a pushing tool, as described hereinbelow. Typically, when the ring is in its expanded state, all of the pivot joints are disposed in a plane that is perpendicular to longitudinal axis 10 of ring 24.

Figure 2B:
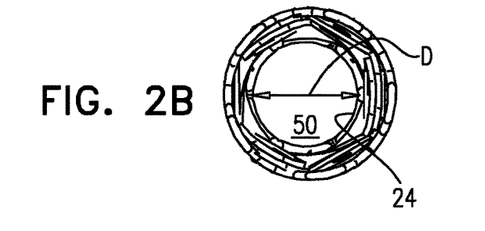

The pivot joints enable the prosthetic valve structure to collapse to form a shape having a generally circular cross-section that defines and surrounds at least in part a central lumen 50, as shown in FIGS. 2A-B. Typically, the pivot joints enable the valve to assume an outer diameter of less than 10 mm, e.g., less than 6 mm (by way of illustration and not limitation), in its collapsed state, as shown in FIG. 2A. Further typically, central lumen 50 (which is defined by ring 24 in its collapsed state) has a cross-sectional length (e.g., diameter D, shown in FIG. 2B) of between 3 mm and 5 mm, the length being measured in a plane that is perpendicular to longitudinal axis 10 of the valve (shown in FIG. 1).

Typically, when used with a trileaflet valve, ring 24 includes six segments 26, such that there are a total of six pivot joints 30 (of which three are upper pivot joints 30U, and three are lower pivot joints 30L), and such that each of the leaflets is disposed between two adjacent upper pivot joints 30U, or two adjacent lower pivot joints 30L. For some applications, the ring includes twelve (or another multiple of six) pivot joints, such that each of the leaflets of a trileaflet valve is disposed between two non-adjacent upper pivot joints 30U, or two non-adjacent lower pivot joints 30L. For some applications, ring 24 is used with a bileaflet valve. For such applications, the ring may include four, eight, or twelve segments 26, such that there are a corresponding number of pivot joints, and such that each of the leaflets is disposed between two of the upper pivot joints or two of the lower pivot joints.

Each of segments 26 of ring 24 is configured to become twisted when the ring is folded, as shown in FIG. 2A. For some applications, due to shape-memory properties of the segments, the segments facilitate the expansion of the ring, since the segments are pre-shaped in non-twisted shapes.

In the collapsed state of the valve, the valve leaflet frame, the valve leaflets, the upper skirt, and the lower skirt are also collapsed. Typically, the valve is configured such that the expansion of the ring causes each of the aforementioned portions to become expanded automatically.

Figure 3:
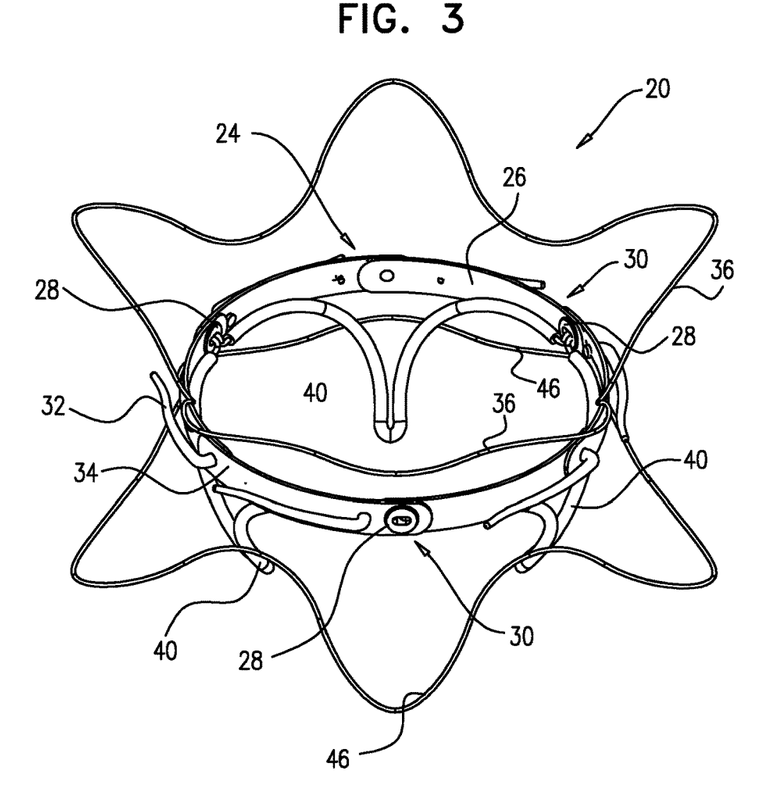
FIG. 3 is a schematic illustration of the prosthetic heart valve of FIG. 1 in an assembled, expanded state, in accordance with some applications of the present invention.

In order to deploy prosthetic valve structure 20 inside the heart, the physician pushes the upper pivot joints 30U distally, using a pushing tool. The pushing of the upper pivot joints enables annular valve ring 24 to expand radially in order for the prosthetic valve structure to assume an expanded state, as shown in FIG. 3. Responsively to the expanding of the prosthetic valve structure, valve leaflet frame 40, valve leaflets 44, upper skirt frame 36, and lower skirt frame 46 also expand from their respective collapsed states.

For some applications, annular valve ring 24 is coupled to a plurality of generally curved, prong-shaped anchors 32, for example, four to eight anchors, e.g., six anchors, as shown by way of illustration and not limitation in FIG. 1. In the expanded state of valve structure 20, as shown in FIG. 3, the anchors are disposed circumferentially and in concentric alignment with the annular valve ring. As shown in FIG. 3, the anchors project from the annular valve ring through the valve ring fabric sleeve 34. As the prosthetic valve structure transitions to a collapsed state, as shown in FIG. 2A, the anchors remain alongside respective segments of the annular valve ring to which each anchor is adjacently disposed in the expanded state of the prosthetic valve structure.

During implantation of prosthetic valve structure 20, a lower portion of the prosthetic valve structure is first advanced toward the ventricular surface of the native valve. Once the distal end of the catheter is positioned in the ventricle of the patient, the physician pushes distally on the upper valve pivot joints 30 in order to (1) expose annular valve ring portion 24 and the lower skirt frame 46 and lower skirt fabric 48 from within the catheter, and (2) in conjunction, expand the annular valve ring. As the annular valve ring expands, lower skirt frame 46, valve leaflet frame 40, and valve leaflets 44 passively (i.e., automatically) expand. As the physician expands the annular valve ring, each of the anchors remain disposed circumferentially with respect to the segment of the annular valve ring to which the anchor is adjacently disposed (as shown in FIG. 3). In such a manner, a space is created between each anchor and the respective segments of the annular valve ring to which each anchor is adjacently disposed.

By pulling proximally on the catheter and the tool coupled to prosthetic valve structure 20 disposed therein, the annular valve ring is positioned adjacent to a ventricular surface of the native valve. Once the valve ring portion is positioned adjacent to the ventricular surface, the physician rotates annular valve ring 24 (e.g., by rotating 30 degrees a tool coupled thereto) about an axis that runs between the native valve from the atrium to the ventricle (which during implantation of the valve, is typically approximately aligned with longitudinal axis 10 of the valve). During this rotation, portions of native chordae tendineae 60 are grasped and placed between each anchor and the respective segment of the annular valve ring to which the anchor is adjacently disposed, as shown in FIG. 4. This grasping of the leaflets provides supplemental support to the prosthetic valve during and following implantation thereof. Alternatively or additionally, support is provided to the prosthetic valve by the upper and lower skirts, and/or by ring 24.

In conjunction with the grasping of the chordae tendineae, the prosthetic valve is secured in place. The physician then pulls the catheter proximally in order to expose upper skirt frame 36 and upper skirt fabric 38 from within the catheter. The skirt then expands over the atrial surface of the native valve in order to create a flush coupling between the prosthetic valve and the native valve.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:
1. Apparatus for use at a native heart valve of a subject, the apparatus comprising:
   an implant, dimensioned for transluminal advancement to the native heart valve, and comprising:

a plurality of metal segments, coupled at a plurality of joints to define a ring in which the plurality of joints alternate between upper joints and lower joints disposed along the ring; and a plurality of anchors, each of the anchors coupled to the ring at a respective one of the joints; and a tool, couplable to the implant, and configured to anchor the implant at the native heart valve by rotation of the anchors, wherein the implant has an implanted state in which the plurality of anchors are arranged circumferentially around the ring, on a plane that is perpendicular to a longitudinal axis of the ring.

2. The apparatus according to claim 1, wherein each of the anchors is curved.

3. The apparatus according to claim 1, wherein each of the anchors is prong-shaped.

4. The apparatus according to claim 1, wherein the tool is further configured to change an angular disposition between adjacent segments of the plurality of segments.

5. The apparatus according to claim 1, wherein the tool is configured to apply a force at at least some of the joints.

6. The apparatus according to claim 1, wherein the plurality of joints facilitates changing of an annular disposition between adjacent segments of the plurality of segments while the implant is disposed at the native heart valve.

7. The apparatus according to claim 1, wherein the tool is configured to change the annular disposition by applying a force at at least some of the joints.

8. The apparatus according to claim 1, wherein the plurality of anchors consists of 4-8 anchors.

9. The apparatus according to claim 1, wherein the implant has a folded state for transluminal delivery, in which the implant has a generally circular cross-section that defines and surrounds at least in part a central lumen.

10. The apparatus according to claim 1, wherein the ring is surrounded by a fabric sleeve.

11. The apparatus according to claim 10, wherein each of the anchors projects from the ring through the fabric sleeve.

12. The apparatus according to claim 1, wherein the implant further comprises a plurality of annular elements, each of the annular elements coupled to the ring at a respective one of the joints.

13. The apparatus according to claim 12, wherein the annular elements facilitate changing of an annular disposition between adjacent segments of the plurality of segments.

14. Apparatus for use at a native heart valve of a subject, the apparatus comprising:
an implant, dimensioned for transluminal advancement to the native heart valve, and comprising:
a plurality of metal segments, coupled at a plurality of joints to define a ring in which the plurality of joints alternate between upper joints and lower joints disposed along the ring;
a plurality of anchors, each of the anchors coupled to the ring at a respective one of the joints; and
a plurality of annular elements, each of the annular elements coupled to the ring at a respective one of the joints; and
a tool, couplable to the implant, and configured to anchor the implant at the native heart valve by rotation of the anchors.

15. The apparatus according to claim 14, wherein each of the anchors is curved.

16. The apparatus according to claim 14, wherein each of the anchors is prong-shaped.

17. The apparatus according to claim 14, wherein the tool is further configured to change an angular disposition between adjacent segments of the plurality of segments.

18. The apparatus according to claim 14, wherein the tool is configured to apply a force at at least some of the joints.

19. The apparatus according to claim 14, wherein the plurality of joints facilitate changing of an annular disposition between adjacent segments of the plurality of segments while the implant is disposed at the native heart valve.

20. The apparatus according to claim 14, wherein the tool is configured to change the annular disposition by applying a force at at least some of the joints.

21. The apparatus according to claim 14, wherein the plurality of anchors consists of 4-8 anchors.

22. The apparatus according to claim 14, wherein the implant has a folded state for transluminal delivery, in which the implant has a generally circular cross-section that defines and surrounds at least in part a central lumen.

23. The apparatus according to claim 14, wherein the ring is surrounded by a fabric sleeve.

24. The apparatus according to claim 23, wherein each of the anchors projects from the ring through the fabric sleeve.

25. The apparatus according to claim 14, wherein the annular elements facilitate changing of an annular disposition between adjacent segments of the plurality of segments.

* * * * *